(12) United States Patent
Noy

(10) Patent No.: US 8,858,626 B2
(45) Date of Patent: Oct. 14, 2014

(54) ACCOMMODATIVE INTRAOCULAR LENS SYSTEM

(75) Inventor: Stephen Van Noy, Southlake, TX (US)

(73) Assignee: Novartis AG, Basel (CH)

( * ) Notice: Subject to any disclaimer, the term of this patent is extended or adjusted under 35 U.S.C. 154(b) by 148 days.

(21) Appl. No.: 12/699,967

(22) Filed: Feb. 4, 2010

(65) Prior Publication Data

US 2010/0204787 A1 Aug. 12, 2010

Related U.S. Application Data

(60) Provisional application No. 61/151,381, filed on Feb. 10, 2009.

(51) Int. Cl.
*A61F 2/16* (2006.01)
(52) U.S. Cl.
CPC .............. *A61F 2/1613* (2013.01); *A61F 2/1629* (2013.01); *A61F 2/1648* (2013.01)
USPC ........................... 623/6.34; 623/6.4; 623/6.43
(58) Field of Classification Search
USPC ............. 623/6.32, 6.34, 6.37, 6.38, 6.4, 6.43, 623/6.51, 6.54
See application file for complete search history.

(56) References Cited

U.S. PATENT DOCUMENTS

| 4,816,030 | A | 3/1989 | Robinson | |
|---|---|---|---|---|
| 6,797,004 | B1 | 9/2004 | Brady et al. | |
| 2002/0002404 | A1 | 1/2002 | Sarfaraz | |
| 2002/0128710 | A1 | 9/2002 | Eggleston | |
| 2003/0114927 | A1 * | 6/2003 | Nagamoto | 623/6.37 |
| 2003/0204255 | A1 * | 10/2003 | Peng et al. | 623/6.34 |
| 2004/0162612 | A1 * | 8/2004 | Portney et al. | 623/6.34 |
| 2004/0236422 | A1 | 11/2004 | Zhang et al. | |
| 2004/0249455 | A1 | 12/2004 | Tran | |
| 2005/0209692 | A1 | 9/2005 | Zhang | |
| 2007/0016293 | A1 * | 1/2007 | Tran | 623/6.34 |
| 2007/0260308 | A1 * | 11/2007 | Tran | 623/6.34 |
| 2008/0051886 | A1 * | 2/2008 | Lin | 623/6.34 |
| 2010/0204788 | A1 * | 8/2010 | Van Noy | 623/6.37 |

\* cited by examiner

*Primary Examiner* — Randy Shay
(74) *Attorney, Agent, or Firm* — Jonathan E. Prejean

(57) ABSTRACT

A two-optic accommodative lens system is disclosed. Two coupled lenses are located within the capsular bag to extend depth of focus and/or restore accommodation following extraction of a natural lens. The first lens comprises a spring-like structure attaching an optic to a ring-like support structure. The optic can be a monofocal or multifocal optical element having a positive or negative power. The first lens further comprises features designed to couple the ring-like structure to a second lens. The first lens can be located anteriorly within the capsular bag. The second lens is located posteriorly to the first lens within the capsular bag and can have an opposite or supplementary power to that of the first lens. The second lens can also be a monofocal or multifocal lens and comprises a plurality of haptics which can be used to size the lens system over a range of capsular bag sizes. The second lens further comprises features for coupling the second lens to the ring-like structure of the first lens. The haptics of the second lens are relatively firm, yet still flexible and can be configured to interlock with features of the ring-like structure.

13 Claims, 4 Drawing Sheets

ACCOMMODATIVE INTRAOCULAR LENS SYSTEM

This application claims priority to U.S. Provisional Application Ser. No. 61/151,381 which was filed on Feb. 10, 2009.

This invention relates generally to the field of intraocular lenses (IOLs) and, more particularly, to accommodative IOLs.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Typically, when a cataract or other disease requires the removal of the natural lens and replacement with an artificial IOL, the IOL is a monofocal lens, requiring that the patient use a pair of spectacles or contact lenses for near vision. Advanced Medical Optics has been selling a bifocal IOL, the Array lens, for several years, but this lens has not been widely accepted. The Bausch and Lomb Crystalens™ accommodative IOL is also available, but has a number of disadvantages.

Several other designs for accommodative IOLs are being studied. For example, see U.S. Pat. Nos. 6,197,059, 5,674,282, 5,496,366 and 5,476,514 (Cumming), the entire contents of which being incorporated herein by reference. The lens described in these patents is a single optic lens having flexible haptics that allow the optic to move forward and backward in reaction to movement of the ciliary muscle. Similar designs are described in U.S. Pat. Nos. 6,302,911 B1 (Hanna), 6,261,321 B1 and 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not inherently resistive to the formation of posterior capsule opacification ("PCO"). The treatment for PCO is a capsulotomy using an Nd:YAG laser that vaporizes a portion of the posterior capsule. Such destruction of the posterior capsule may destroy the mechanism of accommodation of these lenses.

Prior art accommodative lenses also lack extended depth of focus in addition to having poor accommodation performance. Prior art lenses further require precise lens sizing for proper function over a range of capsular bag sizes and lack long term capsular fixation and stability. Lastly, as current lens replacement surgeries move towards smaller incision size, IOLs in general require the ability to be delivered through such small incisions.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system.

Therefore, a need continues to exist for a safe and stable accommodative intraocular lens system that provides accommodation over a broad and useful range.

BRIEF SUMMARY OF THE INVENTION

Embodiments of the present invention improve upon the prior art by providing a two-optic accommodative lens system. Two intraocular lenses are designed to be located within the capsular bag to extend depth of focus and/or restore accommodation following extraction of a natural lens. A first lens comprises a structure attaching an optic to a ring-like support structure. The attachment structure can be a spring-like attachment structure. The optic can be a monofocal or multifocal optical element having a positive or negative power. The first lens further comprises features designed to couple the ring-like support structure to a second lens. The first lens can be located anteriorly within the capsular bag. The second lens is located posteriorly to the first lens within the capsular bag and can have an optic having an opposite or supplementary power to that of the first lens optic. The second lens optic can also be a monofocal or multifocal optical element and the second lens can comprise a plurality of haptics which can be used to size the lens system over a range of capsular bag sizes. The second lens further comprises features for coupling the second lens to the ring-like structure of the first lens. The haptics of the second lens can be firm, yet flexible and can be configured to interlock with features of the ring-like structure. This interlocking capability of the two lenses ensures stable relative fixation of the optical components. Because the ring-like structure of the first lens can be coupled to the second lens, capsular contraction forces operating on the haptics of the second lens, which can extend beyond the ring-like structure, are transferred to the ring-like structure and not to the second lens optic. The second lens optic can thus be made thinner in cross-section as the forces operating on the second lens once it is implanted are smaller than would be the case without the ring-like structure.

The embodiments of the two lens system of this invention having these interlocking features are designed to present a continuous barrier to lens epithelial cell ("LEC") proliferation to minimize Posterior Capsule Opacification ("PCO"). Optic powers of the lenses can be selected to provide between 1 and 10 diopters of depth of focus and/or accommodation as a function of separation distance in response to changes in capsular bag tension related to ciliary muscle movement during accommodation. The ring-like structure of the first lens and related interlocking features can be designed to permit secondary implantation with existing monofocal IOLs.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible accommodative lens system.

These and other advantages and objectives of the present invention will become apparent from the detailed description and claims that follow.

DETAILED DESCRIPTION OF THE INVENTION

Figure 1A:
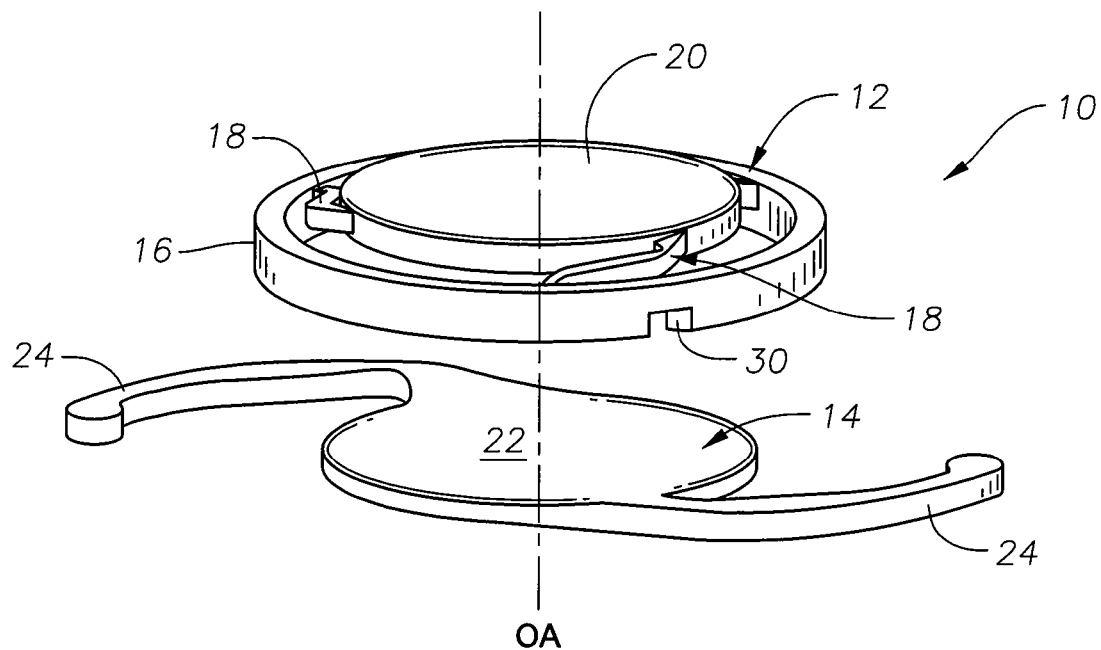
FIG. 1A is an exploded view of an embodiment of the lens system of the present invention showing exemplary ring and lens components, in this embodiment a first lens comprising a ring-like structure with a notched posterior surface and an open-loop second lens design.

As best seen in the FIGUREs, lens system 10 of the present invention generally consists of anterior lens 12 and posterior lens 14. Anterior lens 12 comprises first optic 20, ring 16 and spring-like attachment structures 18. First optic 20 is preferably integrally formed (e.g., as a single-piece) with ring 16 and is connected to ring 16 by one or more spring-like structures 18. Lenses 12 and 14 are preferably made from a soft, foldable material that is resistive to the formation of PCO, such as a soft acrylic, a hydrogel or silicone. First optic 20 can be a monofocal or multifocal optical element having any suitable negative or positive power. Posterior lens 14 comprises a second optic 22. Second optic 22 is located posteriorly to first optic 20 and may also be a monofocal or multifocal optical element and can have any suitable power, but preferably has an opposite or supplementary power to that of first optic 20. Posterior lens 14 comprises a plurality of haptics 24, which can be used to size the lens system 10 over a range of capsular bag sizes. Anterior lens 12 is designed to move along the direction of an optical axis (e.g., axis OA) of an eye in which it is implanted in response to movement of the ciliary muscle, in part due to the spring-like nature of structures 18. Posterior lens 14 is designed to remain in a more fixed position relative to ring 16 and anterior lens 12.

Figure 1B:
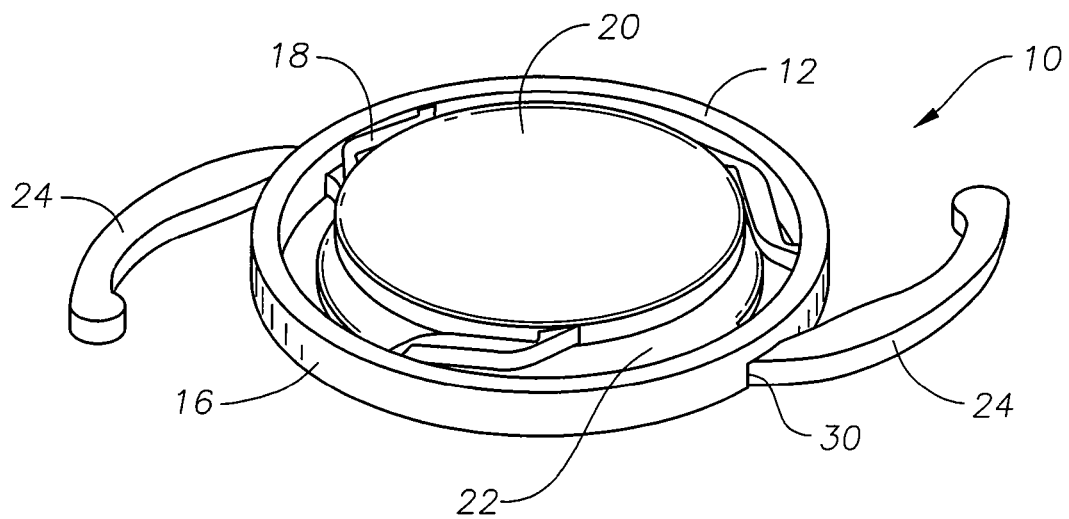
FIG. 1B is a top-view of an embodiment of the lens system of the present invention shown in FIG. 1A with the lenses coupled together.
Figure 2A:
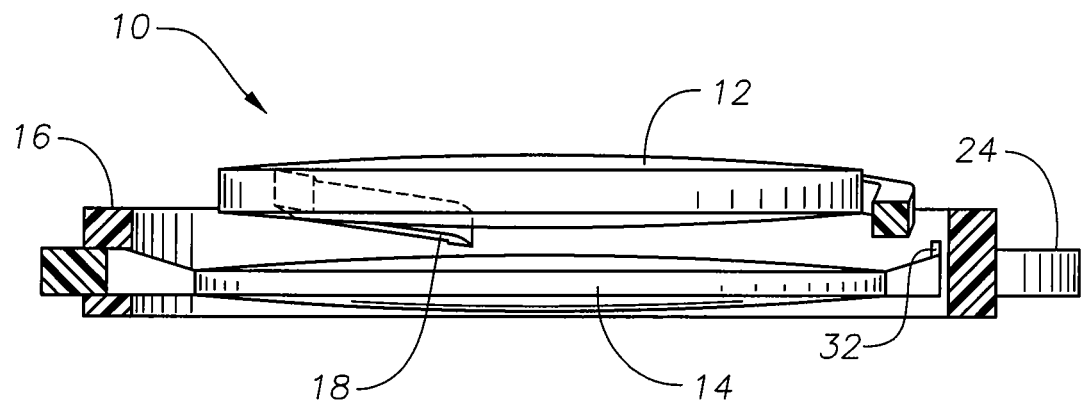
FIG. 2A is an exploded view of an embodiment of the lens system of the present invention showing exemplary ring and lens components, in this embodiment a ring of the first lens having a through-hole for receiving a haptic of the second lens.
Figure 2B:
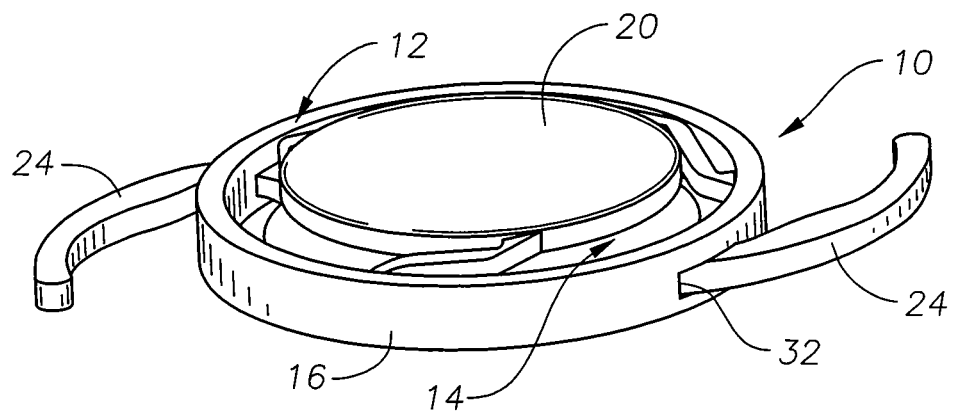
FIG. 2B is a perspective view of the embodiment of the lens system of the present invention shown in FIG. 2A.

Anterior lens 12 further comprises interlock features designed to couple lens 12 to posterior lens 14. These features can comprise notches 30 in the posterior surface of ring 16, as shown in FIGS. 1A and 1B, through-holes 32 in the walls of ring 16, as shown in FIGS. 2A and 2B, notches in the anterior surface of ring 16 (not shown) or a combination of the three interlock features. Other interlock features, as will be known to those having skill in the art, can also be used to couple anterior lens 12 and posterior lens 14.

Anterior lens 12 can be located anteriorly within the capsular bag when implanted. Haptics 24 are firm enough, yet still flexible, so as to allow some, but not excessive, flexing in response to ciliary muscle contraction and relaxation and can be configured to mate with the interlock features of ring 16 to couple anterior lens 12 and posterior lens 14. The complimentary interlocking features of lenses 12 and 14 ensure stable relative fixation of the optical components (e.g., first and second optics 20 and 22). Because the ring-like structure (ring 16) of anterior lens 12 is coupled to posterior lens 14, capsular contraction forces operating on haptics 24, which can extend beyond ring 16, are primarily transferred to ring 16 and not to second optic 22. The second optic 22 can thus be made thinner in cross-section than would otherwise be possible without the presence of ring 16, as the forces operating on second lens 14 are made smaller than would be the case without ring 16.

The relative powers of first optic 20 and second optic 22 can be such that the axial movement of lens 12 toward or away from lens 14 (e.g., of optics 20/22) should be sufficient to adjust the overall power of lens system 10 at least about one diopter and, in some embodiments, at least about three to four diopters. The calculation of the optical powers of lenses 12 and 14 are within the capabilities of one skilled in the art of designing ophthalmic lenses by, for example, using the following equations:

$$P = P_1 + P_2 - T/n \cdot P_1 P_2 \quad (1)$$

$$\delta P = -\delta T/n \cdot P_1 P_2 \quad (2)$$

Wherein, P is the overall power of the lens system, $P_1$ is the optical power of the first optic, $P_2$ is the optical power of the second optic, T is the separation between the optics, and n is the refractive index of the medium between the optics. Equation 2 is the differential of equation 1.

The embodiments of the lens system 10 of the present invention are designed to be implanted and located within the capsular bag to extend depth of focus and/or restore accommodation following extraction of a natural lens. The two lens system and related interlocking features is designed to present a continuous barrier to lens epithelial cell ("LEC") proliferation to minimize PCO. Optic powers of the lenses 12 and 14 can be selected to provide between about 1 and about 10 diopters of depth of focus and/or accommodation as a function of separation distance in response to changes in capsular bag tension related to ciliary muscle movement during accommodation. The first lens ring 16 and related interlocking features can also be designed to permit secondary implantation with existing monofocal IOLs.

Figure 3A:
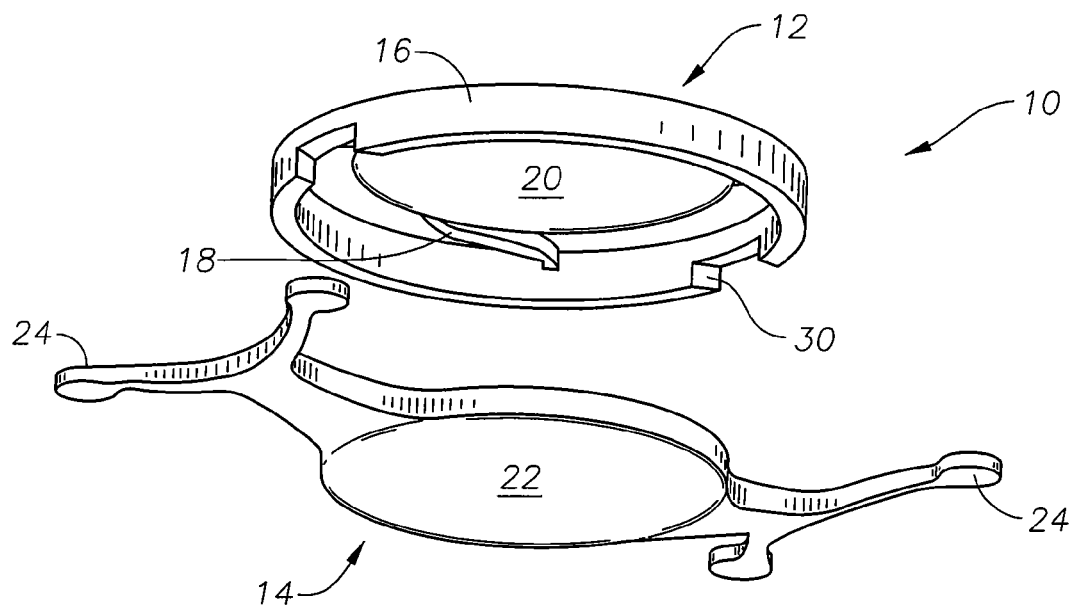
FIGS. 3A and 3B are exploded and assembled views, respectively, of an embodiment of the lens system of the present invention showing exemplary notched ring and lens components, in this embodiment a first lens comprising a ring-like structure having a notched posterior surface and a four-point fixated open loop second lens design.
Figure 3B:
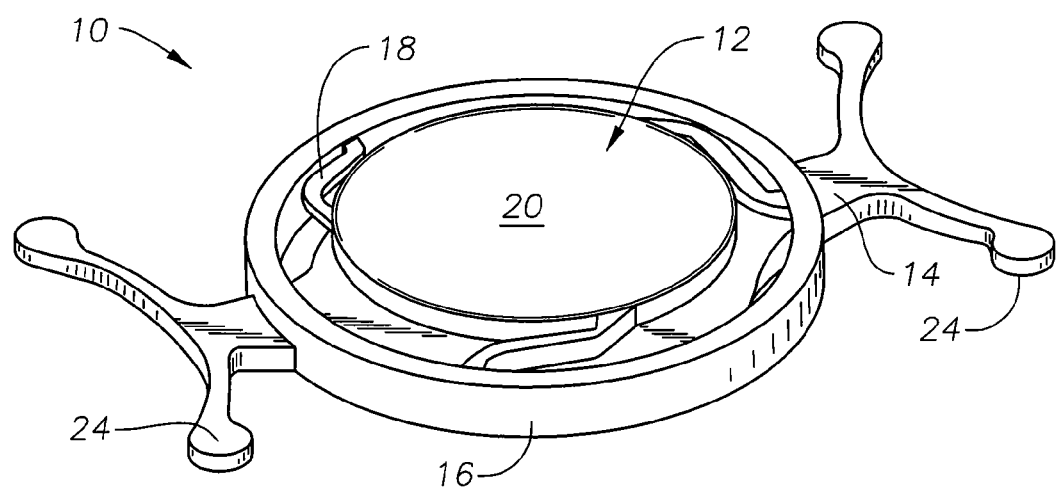

Interlock features of ring 16 (e.g., notches 30, holes 32, or other attachment feature(s)) enable the embodiments of the present invention to couple lens 12 and 14 together such that they can present a continuous lens/ring surface to the posterior capsule with minimal space for lens epithelial cell passage. With respect to embodiment with notches, the continuous surface is created by virtue of the haptics 24 filling the notches 30, as seen in FIGS. 1B and 3B. Lens 12 and lens 14 can be temporarily or permanently joined before or after lens delivery into the eye (implantation). Anterior lens 12 and posterior lens 14 of the embodiments of the present invention can incorporate specialized monofocal, multifocal or varifocal optics including spherical, astigmatism, higher-order, chromatic, combined, refractive surgery induced, and custom aberration correcting designs using refractive and/or diffractive technologies including apodization.

Figure 4A:
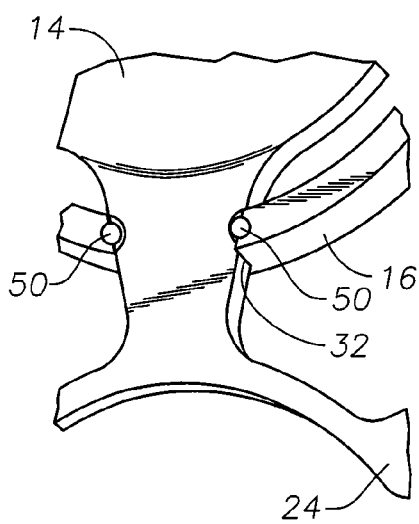
FIGS. 4A and 4B show an enlarged view of one embodiment of the interlocking features of the lens system of the present invention, in this embodiment a ball-detent interlock.
Figure 4B:
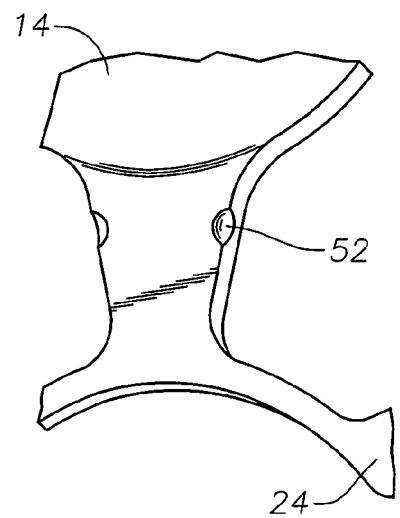
Figure 5A:
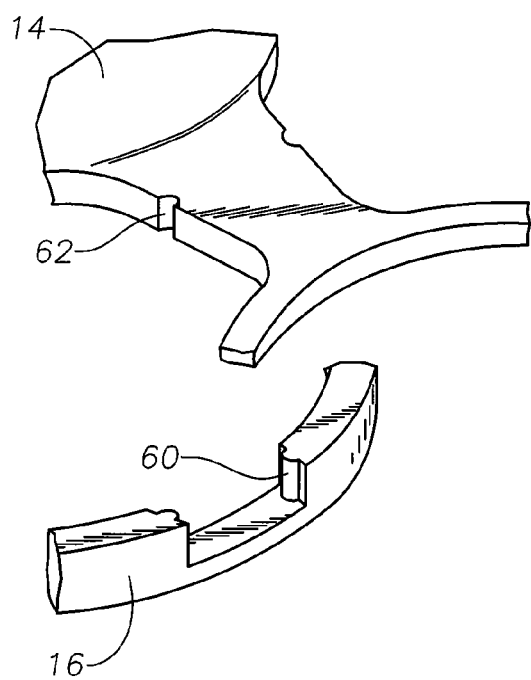
FIGS. 5A and 5B show an enlarged view of another embodiment of the interlocking features of the lens system of the present invention, in this embodiment a tongue-in-groove interlock.
Figure 5B:
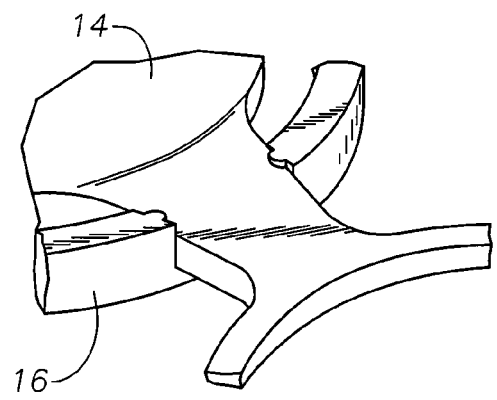

Posterior lens 14 comprises complimentary interlock features to couple with the interlock features of ring 16. Exemplary complimentary interlock features are shown in FIGS. 4-5. In some embodiments, notches 32 of ring 16 can comprise overlaps 50 extending beyond the inner walls of notches 32 such that they overlap haptics 24 when positioned to couple the lenses 12 and 14 together (a ball-detent interlock). As shown in FIGS. 4A and 4B, overlaps 50 can fit into recesses 52 of lens 14 and help to securely hold the two lenses together. In other embodiments, as shown in FIGS. 5A and 5B, notches 32 can comprise protrusions 60 dimensioned to fit into complimentary grooves 62 (a tongue and groove interlock) on the posterior lens 14 haptics 24 to couple the lenses together.

Because ring 16 provides capsular support, second optic 22 can be thinner and still provide optical performance comparable to a thicker optic. The interlock features help ensure that the optic remains stable during capsular contractions and permit a thinner optic element. Further, because the posterior lens 14 haptics 24 can extend beyond the outer diameter of anterior lens 12, this helps prevent sub-luxation into the vitreous humor. Embodiments of the lens system 10 of the present invention thus provide interlocking lenses to help ensure stable relative fixation of the optical components of lens system 10. Because ring 16 and posterior lens 14 are coupled, capsular contraction forces operating on haptics 24 are primarily transferred to the ring 16 and not to second optic 22, allowing for a thinner second optic 22 cross-section. To assist ring 16 in reducing PCO, components of the embodiments of lens system 10 of the present invention can incorporate chemicals, materials and/or specialized features to control PCO or treat ocular diseases, as will be known to those having skill in the art.

In use, posterior lens 14 and anterior lens 12 can be implanted separately. For example, lens 14 can be implanted into the capsular bag prior to the implantation of lens 12. Lens 14 is held within the capsular bag by haptics 24. Lens 12 can then be implanted and the lenses coupled by means of the interlock features discussed above. The sequence of implantation and coupling together of lenses 12 and 14 can vary, as will be known to those having skill in the art and as discussed above.

Embodiments of the lens system of the present invention can thus provide for permanent or temporary attachment of one optic to another permitting image magnification related to relative movement driven by changes in capsular geometry. Further, the interlock points at the interlock features of ring 16 and posterior lens 14 serve to transfer peripheral capsular forces on the haptics 24 of posterior lens 14 (the fixed lens) to ring 16. In this way, the coupled optics can leverage relative movement of the first optic 20 into increased depth of focus over a single element system. Embodiments of the lens system of the present invention further incorporate interlock features, different from the prior art, especially in a way that minimizes lens profile to permit insertion of the lenses through a small incision. Utilizing a notch or through-hole interlock feature permits incorporation of a second optic 22 while maintaining uninterrupted contact of the lens system 10 with the posterior capsule. Haptics 24 help take up slack in the capsular bag which helps address sizing concerns related to accommodating performance and PCO. In addition, the use of a posterior optic provides additional optic stability and added safety against vitreous sub-luxation in the event of intended or unintended disruption of posterior capsule integrity. Embodiments of the present invention can incorporate keying of advanced (toric) optics relative to each other to maintain a desired orientation.

This description is given for purposes of illustration and explanation. It will be apparent to those skilled in the relevant art that changes and modifications may be made to the invention described above without departing from its scope or spirit.

I claim:

1. An accommodative intraocular lens system, comprising:
a) a first lens comprising a first optic, a circular support ring having one or more interlock features, the circular support ring comprising an anterior surface, a posterior surface, and a circular wall extending between the anterior surface and the posterior surface, the interlock features comprising a plurality of notches formed in the circular wall at the posterior surface of the circular support ring, and an attachment structure, the attachment structure coupling the first optic to the circular support ring; and
b) a second lens comprising a second optic and a plurality of haptics, the haptics configured to fit into and fill the notches on the posterior surface of the support ring to couple to the circular support ring at one or more of the interlock features, wherein the haptics extend beyond the support ring when the support ring is coupled to the second lens and wherein the circular support ring is a single ring configured such that when coupled with the second lens the posterior surface of the circular support ring and said haptics contact a posterior side of a capsular bag in an uninterrupted manner when implanted within an eye.

2. The lens system of claim 1, wherein the first lens and the second lens comprise a soft acrylic material.

3. The lens system of claim 1, wherein at least one of the first and second lenses comprise a hydrogel material or a silicone material.

4. The lens system of claim 1, wherein when the first lens and the second lens implanted and coupled in an eye, the interlock features distribute forces applied to the haptics of the second lens so that the first optic responds to changes in the geometry of the eye capsule by moving axially to provide a range of accommodation.

5. The lens system of claim 4, wherein the range of accommodation is between about 1 diopter and about 4 diopters.

6. The lens system of claim 1, wherein the second lens and the support ring couple to form a continuous barrier to lens epithelial cell proliferation.

7. The lens system of claim 1, wherein the first lens is a monofocal lens, a multifocal lens or a varifocal lens.

8. The lens system of claim 1, wherein the second lens is a monofocal lens, a multifocal lens or a varifocal lens.

9. The lens system of claim 1, wherein the second lens is a two-point fixated lens.

10. The lens system of claim 1, wherein the interlock features comprise a ball-detent interlock.

11. The lens system of claim 1, wherein the interlock features comprise a tongue and groove interlock.

12. The lens system of claim 1, wherein the second optic has an opposite or supplementary power to that of the first optic.

13. The lens system of claim 1, wherein the first optic and second optic have optical powers selected to provide a range of accommodation between about 1 diopter and about 10 diopters.

* * * * *